(12) United States Patent
Park et al.

(10) Patent No.: US 7,375,243 B2
(45) Date of Patent: May 20, 2008

(54) METHOD FOR PREPARATION OF AMINO ACID CHELATE

(75) Inventors: Myung-Gyu Park, Yongin Si (KR); Mi Hee Choi, Suwon-si (KR)

(73) Assignee: MD Bioalpha Co., Ltd. (KR)

( * ) Notice: Subject to any disclaimer, the term of this patent is extended or adjusted under 35 U.S.C. 154(b) by 42 days.

(21) Appl. No.: 10/537,409

(22) PCT Filed: Dec. 5, 2003

(86) PCT No.: PCT/KR03/02674

§ 371 (c)(1),
(2), (4) Date: Nov. 25, 2005

(87) PCT Pub. No.: WO2004/050664

PCT Pub. Date: Jun. 17, 2004

(65) Prior Publication Data

US 2006/0128799 A1      Jun. 15, 2006

(30) Foreign Application Priority Data

Dec. 5, 2002   (KR) .................. 10-2002-0076803

(51) Int. Cl.
  *C07F 13/00* (2006.01)
  *C07F 3/00* (2006.01)
  *C07F 15/00* (2006.01)
  *A61K 8/37* (2006.01)

(52) U.S. Cl. .................. 556/50; 556/134; 556/138; 424/401

(58) Field of Classification Search .......... 556/50, 556/134, 148, 138; 424/401
See application file for complete search history.

(56) References Cited

U.S. PATENT DOCUMENTS

| 4,599,152 | A |   | 7/1986 | Ashmead |
| 4,830,716 | A | * | 5/1989 | Ashmead ............ 205/457 |
| 6,458,981 | B1 |  | 10/2002 | Ashmead et al. |
| 2004/0077714 | A1 | * | 4/2004 | Abdel-Monem et al. .... 514/492 |

OTHER PUBLICATIONS

International Search Report; International Application No. PCT/KR2003/002674; Date of Actual Completion Mar. 15, 2004; Date of Mailing Mar. 16, 2004; 2 pages.

* cited by examiner

*Primary Examiner*—Porfirio Nazario-Gonzalez
(74) *Attorney, Agent, or Firm*—Cantor Colburn LLP

(57) ABSTRACT

The present invention provides methods for preparation of metallic amino acid chelates that are electrically neutral and free of interfering ions, by reacting a metal carbonate and an acidic amino acid in an aqueous solution, and the uses of said metallic amino acid chelates. The metallic amino acid chelates can be added to a product such as medical supplies, foods, beverages, cosmetics, feeds, etc., with maintaining the stability of the product at a variety of temperature and pH ranges and also having no effect on the properties of the product, including taste and appearance.

13 Claims, No Drawings

METHOD FOR PREPARATION OF AMINO ACID CHELATE

FIELD OF THE INVENTION

The present invention relates to methods for preparation of amino acid chelates and the uses of the same, and more specifically, to methods of preparing metallic amino acid chelates that are electrically neutral and free of interfering ions, by reacting a metal carbonate and an acidic amino acid in an aqueous solution, and the uses of said metallic amino acid chelates.

BACKGROUND OF THE INVENTION

In general, an advantage of amino acid chelates is the fact that they are readily absorbed into absorptive mucosal cells or plant cells by means of active transport or other known mechanisms. In other words, where minerals are absorbed along with amino acids as carrier molecules, it is possible to avoid problems associated with the competition of ions for active sites and the suppression of specific nutritive mineral elements by others.

Amino acid chelates are generally made by reacting alpha-amino acids and metal ions, where the metal ion has a valence of 2 or more, to form a ring structure in a chelate. In such a reaction, the cationic charge of the metal ion is neutralized by the free amino group or carboxyl group of the alpha-amino acid.

These metallic amino acid chelates are represented as the formula below.

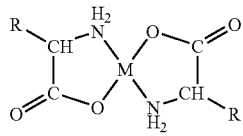

wherein M is a divalent metal ion, and R is a side chain of naturally occurring amino acids or peptides. The metal ion includes, for example, calcium, zinc, magnesium, copper, iron, cobalt, manganese, chromium, etc.

Typically, the term "chelate" is defined as a combination of a metal ion and one or more ligands bonded thereto to form a heterocyclic ring structure. In accordance with a definition in the American Association of Feed Control Officials ("AAFCO"), "amino acid chelate" is a product resting from the reaction of a metal ion from a soluble metal salt with amino acids at a molar ratio of two or three moles of amino acid to one mole of metal to form coordinate covalent bonds. In general, the average weight of the hydrolyzed amino acids must be approximately 150 and the resulting molecular weight of the chelate must not exceed 800.

The structure, chemistry and the bioavailability of amino acid chelates are described in a variety of documents, for example, Ashmead et al., Chelated Mineral Nutrition, (1982), Chas. C. Thomas Publishers, Springfield, III.; Ashmead et al., Intestinal Absorption of Metal Ions, (1985); Ashmead et al., Foliar Feeding of Plants with Amino Acid Chelates, (1986); U.S. Pat. No. 4,020,158; U.S. Pat. No. 4,167,564; U.S. Pat. No. 4,216,143; U.S. Pat. No. 4,721,644; U.S. Pat. No. 4,599,152; U.S. Pat. No. 4,774,089; U.S. Pat. No. 4,830,716; U.S. Pat. No. 4,863,898; U.S. Pat. No. 4,725,427 etc.

For reference, it should be understood that the terms "mineral" and "metal ion" as described in this disclosure are used interchangeably.

In the existing methods for preparation of amino acid chelates, where a water soluble salt such as mineral chlorides or sulfates is employed, the reaction condition must be alkaline to more easily perform the reaction. In this case, byproducts tend to be contained in amino acid chelates which may interfere with the synthesis of amino acid chelates or have a negative effect on the absorption thereof in vivo. The reaction formula below as a known method is referred to.

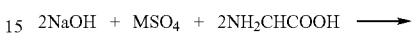
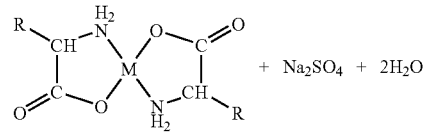

wherein M is a divalent metal ion, and R is a side chain of naturally occurring amino acids or peptides.

Even though the above method provides an electrically neutral amino acid chelate, sulfuric acid dissociates to form anionic sulfate ions and this byproduct interferes with the overall reaction, regardless of whether or not it is present in the form of alkali metal salt and whether or not the sulfate ion takes part in the reaction, and also hinders the adsorption of chelate, per se, in vivo. Moreover, this byproduct is very difficult to separate from the product because the sodium sulfate is water soluble. Furthermore, the reaction of metal sulfate and amino acids does not proceed to 100% completion, thus the sulfuric acid is always present in the reaction system. The same holds true for the presence of chloride ion when utilizing a metal chloride salt, e.g., $MCl_2$, for amino acid chelate preparation.

U.S. Pat. Nos. 6,407,138 and 6,458,981 employ calcium hydroxide and calcium oxide instead of sodium hydroxide, thereby providing an amino acid chelate free of byproducts, but it cannot practically be said that the resulting amino acid chelate is electrically neutral.

The reaction mechanism in U.S. Pat. No. 6,407,138 as mentioned above is represented below.

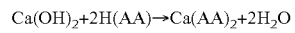

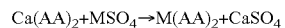

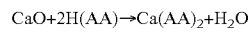

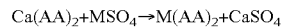

The reaction mechanism in U.S. Pat. No. 6,458,981 as mentioned above is represented below.

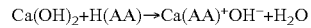

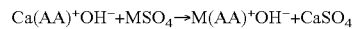

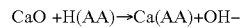

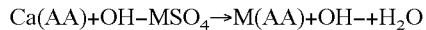

In the above reaction formulas, "AA"s are an amino acid and "M"s are a metal ion.

Referring to these reaction mechanisms, where an amino acid chelate is prepared using calcium hydroxide or calcium oxide, a reaction mixture comprising an electrically neutral amino acid chelate, a cationic amino acid chelate and an anionic hydroxyl group is obtained. Accordingly, it cannot practically be said that the amino acid chelate obtained from these reactions is electrically neutral, as stated previously.

SUMMARY OF THE INVENTION

Accordingly, the object of the present invention is to solve the aforementioned problems encountered in the prior art.

That is, an object of the present invention is to provide a method for preparation of amino acid chelates by a novel process of reacting a naturally occurring or synthetic metal carbonate with an amino acid in an aqueous solution. According to this method, a variety of amino acid chelates that are electrically neutral and free of interfering ions can easily be prepared without the production of byproducts.

Another object of the present invention is to provide a method for preparation of amino acid chelates by additionally reacting a metal sulfate during or after the above reaction procedure, wherein the amino acid chelate comprises a metal ion derived from the metal sulfate and simultaneously different from a metal ion of the metal carbonate.

Still another object of the present invention is to provide a variety of amino acid chelates obtained from the above methods.

Still yet another object of the present invention is to provide compositions containing the above amino acid chelates as an active ingredient in a therapeutically effective amount, a sitologically effective amount or a cosmetically effective amount. These compositions can be used for formulations of drugs, foods, beverages, cosmetics and the like depending upon the uses thereof.

To accomplish the foregoing objects and advantages, the present invention provides a method comprising the step of reacting a naturally occurring or synthetic metal carbonate with an acidic amino acid in an aqueous solution to produce amino acid chelates.

A metal carbonate useful for the preparation method according to the present invention is not particularly limited and includes carbonates of metals with a valence of 2 or more such as calcium, copper, zinc, iron, chromium, cobalt, manganese, magnesium, etc. Exemplary metal carbonates include calcium carbonate, copper carbonate, zinc carbonate, ferrous carbonate, cobalt carbonate, chromium carbonate, magnesium carbonate, manganese carbonate, etc. In some embodiments, a combination of two or more metal carbonates as described above may be used.

The metal carbonate to be used in the present invention may be naturally occurring metal carbonates, synthetic metal carbonates, or a combination thereof. Particularly, the naturally occurring metal carbonates are more preferable because they contain a variety of minerals.

Calcium carbonate, one of metal carbonates useful for the preparation method of the present invention, is briefly discussed herein below.

At present, naturally occurring or synthetic calcium carbonates are applied to many uses and representative examples thereof are their use as additives for calcium-containing foods such as milk, beverages, cookies, snacks and the like. However, calcium being in the form of calcium carbonate is dispersed in water but not completely dissolved, whereby it cannot be applied to the preparation of clear foods such as beverages. Moreover, it tends to be precipitated with the lapse of time, thereby the water-dispersed form has limited applications to many foods.

While naturally-occurring calcium carbonates have a merit of containing a variety of minerals as stated previously, they simultaneously have demerits of a low solubility and low absorptivity in vivo owing to their inorganic properties.

The naturally occurring calcium carbonates are contained, for example, in eggshell calcium, cuttlebone calcium, shell calcium (originated from shells of clam, oyster, etc), seaweed calcium, etc. Of these, the seaweed calcium is a calcium source obtained from calcified seaweeds (phymatolithon calcareum known as "lithothannion") and contains calcium carbonate and magnesium carbonate as major components. The components of seaweed calcium and whey calcium are listed in TABLE 1 as below, respectively, wherein the whey calcium is present in milk and comprises calcium phosphate but not calcium carbonate.

TABLE 1

|  | Seaweed calcium | Whey calcium |
| --- | --- | --- |
| Calcium | 34% | 26.4% |
| Magnesium | 3.2% | 1.26% |
| Sulfur | 0.3% | — |
| Sodium | 0.2% | 2.6% |
| Phosphorous | 0.06% | 14.6% |
| Iron | 0.08% | 0.00815% |
| Potassium | 0.04% | 0.165% |
| Manganese | 70 ppm | — |
| Boron | 25 ppm | — |
| Iodide | 20 ppm | — |
| Zinc | 22 ppm | — |
| Selenium | 1 ppm | — |

As seen in TABLE 1 as above, the seaweed calcium contains magnesium and calcium at a ratio of approximately 1:10 (magnesium:calcium) and little phosphorous. Differently from general calcium stocks including synthetic calcium carbonate, the seaweed calcium contains a variety of minerals which promote the physiological function of calcium. However, even when such naturally occurring calcium carbonates are employed as a calcium source, the problem of insolubility cannot be solved, as stated previously, thereby restricting the extension of uses thereof. Meanwhile, when calcium carbonates contained therein are converted to metallic amino acid chelates like in the present invention, a high absorption rate in vivo can be achieved due to the solubility of the chelate per se, which is proved by EXAMPLES as will be illustrated later herein.

Acidic amino acids useful for the preparation method according to the present invention are not particularly limited and include, for example, glutamic acid, aspartic acid, etc. In some embodiments, a combination of two or more amino acids may be employed.

The amount of metal carbonate and acidic amino acid used in the reaction can be determined depending upon various parameters such as the valence of metal, the reactivity of salt, the reactivity of amino acid, etc., and is preferably in the range of a molar ratio of 1:1~1:4 (metal carbonate:acidic amino acid).

The reaction for synthesis of the amino acid chelate where a metal ion with a valence of 2 is used as the metal carbonate can be illustrated in REACTION FORMULA 1 as below.

Reaction Formula 1

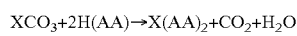

$$XCO_3 + 2H(AA) \rightarrow X(AA)_2 + CO_2 + H_2O$$

wherein, X is a divalent metal ion and AA is an amino acid.

The reaction for synthesis of the amino acid chelate where a metal ion with a valence of 3 is used as the metal carbonate can be illustrated in REACTION FORMULA 2 as below.

Reaction Formula 2

$$X'_2(CO_3)_3 + 6H(AA) \rightarrow 2X'(AA)_3 + 3CO_2 + 3H_2O$$

wherein, X' is a trivalent metal ion and AA is an amino acid.

As can be seen in these reaction formulas, according to the preparation method of the present invention, sulfuric acid as a reaction inhibitor is not created, and the generated byproducts do not affect a desired product and reaction procedure because they are volatile carbon dioxide and water, and the desired product can readily be separated, and the resulting product is electrically neutral.

In the preparation method of the present invention, the reaction of metal carbonate and acidic amino acid is performed in an aqueous solution, wherein water is desirably used as a medium for the aqueous solution, but is not particularly limited thereto so long as the reaction medium does not affect the reaction mechanism and can easily be separated from the product Furthermore, other known materials for increasing the rate and efficiency of reaction may be added to the water or other reaction medium.

The temperature of reaction is preferably in the range of 0~100° C. and if the temperature is excessively low, the reactivity becomes low, whereas if the temperature is excessively high, energy is wasted and deterioration of some amino acids can occur.

The pH of reaction is preferably adjusted to 4~7 to ensure the smooth progress of the reaction and to maintain neutrality, and more preferably to 4.5~6.5.

In some embodiments, a metal sulfate may be added to a reaction system where a metal carbonate is reacted with an acidic amino acid in an aqueous solution, as described above, when the reaction is initiated, or during the reaction, or after completion of the reaction In order to prevent direct reaction of the metal sulfate and the amino acid, the metal sulfate is preferably added during the reaction, and more preferably after completion of the reaction.

The metal sulfate useful for the preparation method according to the present invention includes, for example, but is not limited to calcium sulfate, magnesium sulfate, zinc sulfate, copper sulfate, ferrous sulfate, manganese sulfate, chromium sulfate, cobalt sulfate, etc.

The amount of metal sulfate additionally added to the reaction is desirably at a molar ratio of 1:1~1:4 (metal sulfate:amino acid chelate derived from metal carbonate).

The temperature and pH in the additional reaction of metal sulfate are the same as or very similar to those of the reaction of metal carbonate, as described previously.

Where a metal ion (X) in a metal carbonate salt has a valence of 2 as in REACTION FORMULA 1 and a metal sulfate comprising a metal ion (M) with a valence of 2 other an the metal ion (X) is employed, this additional reaction is as illustrated in REACTION FORMULA 3, blow.

Reaction Formula 3

$$XCO_3 + 2H(AA) + MSO_4 \rightarrow M(AA)_2 + CO_2 + H_2O + XSO_4$$

wherein, X is a divalent metal ion, and M is a divalent metal ion other than X, and AA is an amino acid.

Where a metal sulfate of a metal ion (M') with a valence of 3 is employed, this additional reaction is as illustrated in REACTION FORMULA 4, below.

Reaction Formula 4

$$3XCO_3 + 6H(AA) + M'_2(SO_4)_3 \rightarrow 2(M'(AA)_3) + 3CO_2 + 3H_2O + 3XSO_4$$

wherein, X is a divalent metal ion, and M' is a trivalent metal ion, and AA is an amino acid.

Where a metal carbonate and metal sulfate are subsequently reacted, in other words, the metal carbonate first reacts with an acidic amino acid and then the metal sulfate reacts with a resulting product, an amino acid chelate based upon the metal carbonate is converted to an amino chelate based upon the metal sulfate. Such subsequent reaction is illustrated, for instance, in REACTION FORMULA 5 as below.

Reaction Formula 5

$$XCO_3 + 2H(AA) \rightarrow X(AA)_2 + CO_2 + H_2O \quad (1)$$

$$X(AA)_2 + MSO_4 \rightarrow M(AA)_2 + XSO_4 \quad (2)$$

wherein, X is a divalent metal ion, and M is a divalent metal ion other than X, and AA is an amino acid.

Preferably, the metal carbonate is calcium carbonate and the metal sulfate is a metal sulfate of a metal ion with a valence of 2 other than calcium ion. Accordingly, where the metal carbonate is calcium carbonate and the metal sulfate comprises a divalent metal ion and the calcium amino acid chelate is subsequently reacted with metal sulfate, the reaction is illustrated in REACTION FORMULA 6 as below.

Reaction Formula 6

$$CaCO_3 + 2H(AA) \rightarrow Ca(AA)_2 + CO_2 + H_2O \quad (1)$$

$$Ca(AA)_2 + MSO_4 \rightarrow M(AA)_2 + CaSO_4\downarrow \quad (2)$$

wherein, M is a divalent metal ion other than calcium ion, and AA is an amino acid.

Further, where calcium carbonate and a metal sulfate with a valence of 2 simultaneously react with an amino acid, such a reaction is illustrated in REACTION FORMULA 7 as below.

Reaction Formula 7

$$3CaCO_3 + 6H(AA) + M'_2(SO_4)_3 \rightarrow 2(M'(AA)_3) + 3CO_2 + 3H_2O + 3CaSO_4$$

wherein, M' is a trivalent metal ion, and AA is an amino acid.

In the above reaction formulae, calcium sulfate can easily be separated from a reaction mixture containing other metal sulfates.

As can be seen from the description so far, an amino acid chelate containing a metal (M) other than calcium can be made by a direct method of reacting the carbonate of the metal (M) with an amino acid, or by an indirect method of synthesizing a calcium amino acid chelate and subsequently reacting the sulfate of the metal (M) with the calcium amino acid chelate, wherein the latter, i.e., the indirect method is more desirable in view of reactivity, easy separation of byproducts, etc., in spite of being a relatively more complicated procedure.

The present invention also provides amino acid chelates as represented in FORMULAS 1 and 2 as below, respectively, which are prepared by the above methods.

Formula 1

$$M(AA)_2$$

wherein, M is a divalent metal ion, and AA is an amino acid.

Formula 2

wherein, M' is a trivalent metal ion, and AA is an amino acid.

Amino acid mineral chelates which can be prepared by methods according to the present invention include, for example, but are not limited to calcium glutamate/aspartate, calcium bisglutamate, calcium bisasparate, copper glutamate/aspartate, copper bisglutamate, copper bisaspartate, zinc glutarate/aspartate, zinc bisglutamate, zinc bisaspartate, iron glutamate/aspartate, iron bisglutamate, iron bisaspartate, iron bisglutamate/aspartate, iron glutamate/bisaspartate, chromium glutamate/aspartate, chromium bisglutamate, chromium bisaspartate, chromium bisglutamate/aspartate, chromium glutamate/bisaspartate, cobalt glutamate/aspartate, cobalt bisglutamate, cobalt bisaspartate, magnesium glutamate/aspartate, magnesium bisglutamate, magnesium bisaspartate, manganese glutamate/aspartate, manganese bisglutamate, manganese bisaspartate, or a mixture of two or more of these materials.

The present invention also provides compositions containing amino acid chelates of FORMULAS 1 and/or 2 as an active ingredient at a therapeutically effective amount, a sitologically effective amount or a cosmetically effective amount.

The amino acid chelates of FORMULAS 1 and 2 can be formulated to various dosage forms of pharmaceutical composition depending upon their intended use. More specifically, in preparation of a pharmaceutical composition according to the present invention, the amino acid chelates of FORMULAS 1 and/or 2 as active ingredients can be mixed with a pharmaceutically acceptable carrier, including diluents, excipients, etc., depending upon a required formulation. For example, the pharmaceutical composition according to the present invention can be formulated to drugs for oral or injection administration.

The amino acid chelates of FORMULAS 1 and 2 as active ingredients can be formulated to one dosage unit or multi-dosage unit by known techniques using pharmaceutically acceptable excipients. Drugs may be prepared in the form of solution, suspension or emulsion in an oil or aqueous medium and may contain conventional suspending agent, emulsifying agent or stabilizer. Furthermore, drugs may be prepared in the form of dry powder which will be dissolved in sterile water free of pyrogen prior to use thereof. The amino acid chelates of FORMULAS 1 and 2 may also be formulated to suppository using conventional suppository agents such as cocoa butter or glycerides. Solid drugs for oral administration can be made in the form of capsules, tablets, pills, powders, etc. in which the tablets and pills are particularly useful. The solid drugs can be manufactured by mixing the amino acid chelates of FORMULAS 1 and/or 2 with one or more inactive diluents such as sucrose, lactose, starch or the like, a lubricant such as magnesium stearate, other carriers such as disintegrating agent or coupling agent, etc.

If necessary, the amino acid chelates of FORMULAS 1 and/or 2 or a composition containing them as an active ingredient may be administered together with other drugs.

The term "therapeutically effective amount" as used herein refers to that amount of the compound being administered which will prevent, alleviate or ameliorate to some extent one or more of the symptoms of the disorder being treated. The therapeutically effective amount can be experientially determined by use of well-known in vivo and in vitro model systems pertaining to the disorders being treated.

In the case of formulation as one dosage unit, the amino acid chelates of FORMULAS 1 and/or 2 as active ingredients are preferably contained at an amount of 0.1~1000 mg per dose. The administration on amount of drug can be determined by a physician in consideration of the weight, age, disease state and the like of a patient. The administration amount necessary for treatment of an adult is generally about 1~1000 mg per day depending upon the frequency and intensity of administration. On muscular or vascular administration, about 1~500 mg per day is sufficient for an average adult male but a larger amount may be preferable for some patients.

The term "sitologically effective amount" as used herein refers to the amount of the active ingredient which is useful to improve the metabolic functioning of a patient and also which does not cause any adverse side effects.

The term "cosmetically effective amount" as used herein refers to the amount of the active ingredient which is effective to improve the beauty-related conditions such as skin condition, hair condition, etc. and also which does not does not cause any adverse side effects.

The sitologically effective amount and cosmetically effective amount can be determined by a variety of parameters such as uses and properties of the composition, thus they are not particularly limited.

As a result, the compositions according to the present invention can be applied to various uses including, for example, a pharmaceutical composition comprising an active ingredient and a pharmaceutically acceptable carrier, a food or beverage composition comprising an active ingredient and a sitologically acceptable carrier; and a cosmetics composition comprising an active ingredient and a cosmetically acceptable carrier, in which the active ingredients are the compounds of FORMULAS 1 and/or 2, respectively.

DESCRIPTION OF THE PREFERRED EMBODIMENTS

Hereinafter, the present invention will be described in more detail by EXAMPLES, but the scope of the present invention is not limited thereto.

EXAMPLE 1

Preparation of Seaweed Calcium-Glutamic Acid Chelate 20 g of seaweed calcium (calcium content: 32%) was dispersed in 500 ml of water and dissolved therein by stirring, and 60 g of glutamic acid was added thereto to perform a reaction, then the solution was continually stirred until the seaweed calcium and glutamic acid were entirely dissolved. Bubbles were generated in the initial stage of the reaction but they disappeared after a certain time. The resulting reaction solution was centrifuged to remove insoluble materials, and the clear supernatant was separated. The supernatant was freeze-dried to obtain about 75 g of seaweed calcium-glutamic acid chelate (calcium content: 7%).

The components of the seaweed calcium-glutamic acid chelate obtained thus were analyzed using ICP and the results are listed in TABLE 2 below.

TABLE 2

| Component | Content |
|---|---|
| Calcium | 7% |
| Magnesium | 1% |
| Potassium | 2.1% |
| Sodium | 1% |
| Aluminum | 25 ppm |
| Manganese | 25 ppm |
| Iron | 20 ppm |
| Zinc | 10 ppm |
| Barium | 4 ppm |
| Cadmium, chromium, Molybdenum, cobalt | <5 ppm |

EXAMPLE 2

Preparation of Zinc-Glutamic Acid Chelate 20 g of seaweed calcium (calcium content: 32%) was dispersed in 500 ml of water and dissolved by stirring, and 60 g of glutamic acid was added thereto to perform a reaction, then the solution was continually stirred until the seaweed calcium and glutamic acid were entirely dissolved. Next, 36 g of zinc sulfate (zinc content: 35%) was added to the reaction mixture, and a white precipitate of calcium sulfate was formed. After incubating the reaction for 30 minutes, the reaction solution was centrifuged to remove insoluble materials, and the clear supernatant was separated. The supernatant was freeze-dried to obtain about 70 g of soluble zinc-glutamic acid chelate.

EXAMPLE 3

Preparation of Manganese-Glutamic Acid Chelate 20 g of seaweed calcium (calcium content: 32%) was dispersed in 500 ml of water and dissolved therein by stirring, and 60 g of glutamic acid was added thereto to perform a reaction, then the solution was continually stirred until the seaweed calcium and glutaric acid were entirely dissolved. Next, 30 g of manganese sulfate (manganese content: 27%) was added to the reaction mixture, and a white precipitate of calcium sulfate was formed. After incubating the reaction for 30 minutes, the resulting solution was centrifuged to remove insoluble materials, and the clear supernatant was separated. The supernatant was free-dried to obtain about 68 g of a soluble zinc-glutamic acid chelate.

EXAMPLE 4

Preparation of Copper-Glumatic Acid Chelate 20 g of seaweed calcium (calcium content: 32%) was dispersed in 500 ml of water and dissolved therein by stirring, and 60 g of glutamic acid was added thereto to perform a reaction, then the solution was continually stirred until the seaweed calcium and glutamic acid were entirely dissolved. Next, 30 g of copper sulfate (copper content: 25%) was added to a chelate reaction obtained thus with being stirred to perform a reaction, and a white precipitate of calcium sulfate was formed. After incubating the reaction for 30 minutes, the resulting solution was centrifuged to remove insoluble materials, and the clear supernatant was separated. The supernatant was freeze-dried to obtain about 65 g of soluble copper-glutamic acid chelate.

EXAMPLE 5

Preparation of Iron-Glutamic Acid Chelate 20 g of seaweed calcium (calcium content: 32%) was dispersed in 500 ml of water and dissolved therein by stirring, and 60 g of glutamic acid was added thereto to perform a reaction, then the solution was continually stirred until the seaweed calcium and glutamic acid were entirely dissolved. Next, 30 g of ferrous sulfate (iron content: 20%) was added to the reaction mixture, and a white precipitate of calcium sulfate was formed. After incubating the reaction for 30 minutes, the resulting solution was centrifuged to remove insoluble materials, and the clear supernatant was separated. The supernatant was freeze-dried to obtain about 62 g of soluble iron-glutaric acid chelate.

EXAMPLE 6

Preparation of Magnesium-Glutamic Acid Chelate 20 g of seaweed calcium (calcium content: 32%) was dispersed in 500 ml of water and dissolved therein by stirring, and 60 g of glutamic acid was added thereto to perform a reaction, then the solution was continually stirred until the seaweed calcium and glutamic acid were entirely dissolved. Next 30 g of magnesium sulfate (magnesium content: 9.86%) was added to the reaction mixture, and a white precipitate of calcium sulfate was formed. After incubating the reaction over 30 minutes, the resulting solution was centrifuged to remove insoluble materials, and the clear supernatant was separated. The supernatant was freeze-dried to obtain about 61 g of soluble magnesium-glutamic acid chelate.

EXAMPLE 7

Preparation of Chromium-Glutamic Acid Chelate 20 g of seaweed calcium (calcium content: 32%) was dispersed in 500 ml of water and dissolved therein by stirring, and 60 g of glutamic acid was added thereto to perform a reaction, then the solution was continually stirred until the seaweed calcium and glutamic acid were entirely dissolved. Next, 30 g of chromium sulfate (chromium content: 19%) was added to a chelate reaction obtained thus with being stirred to perform a reaction, a white precipitate of calcium sulfate was formed. After incubating the reaction for 30 minutes, the resulting solution was centrifuged to remove insoluble materials, and the clear supernatant was separated. The supernatant was freeze-dried to obtain about 64 g of soluble chromium-glutamic acid chelate.

EXAMPLE 8

Preparation of Mineral Complex-Glutamic Acid Chelate 20 g of seaweed calcium (calcium content: 32%) was dispersed in 500 ml of water and dissolved therein by stirring, and 60 g of glutamic acid was added thereto to perform a reaction, then the solution was continually stirred until the seaweed calcium and glutamic acid were entirely dissolved. Next 10 g of zinc sulfate (zinc content: 19%), 2 g of manganese sulfate, 2 g of copper sulfate and 2 g of ferrous sulfate were added to the reaction mixture with stirring, and a white precipitate of calcium sulfate was formed. After incubating the reaction for 30 minutes, the resulting solution was centrifuged to remove insoluble materials, and the clear supernatant was separated. The supernatant was freeze-dried to obtain about 65 g of soluble mineral complex-glutamic acid chelate.

EXAMPLE 9

Preparation of Seaweed Calcium-Aspartic Acid Chelate 20 g of seaweed calcium (calcium content: 32%) was dispersed in 500 ml of water and dissolved therein by stirring, and 60 g of aspartic acid was added thereto to perform a reaction, then the solution was continually stirred until the seaweed calcium and aspartic acid were entirely dissolved. Bubbles were generated in the initial stage of the reaction but they disappeared after a certain time. The resulting reaction solution was centrifuged to remove insoluble materials, and the clear supernatant was separated. The supernatant was freeze-dried to obtain about 72 g of seaweed calcium-aspartic acid chelate.

EXAMPLE 10

Preparation of Zinc-Aspartic Acid Chelate 20 g of seaweed calcium (calcium content: 32%) was dispersed in 500 ml of water and dissolved therein by stirring, and 60 g of aspartic acid was added thereto to perform a reaction, then the solution was continually stirred until the seaweed calcium and aspartic acid were entirely dissolved. Next 30 g of zinc sulfate (zinc content: 35%) was added to the reaction mixture, and a white precipitate of calcium sulfate was formed. After incubating the reaction mixture for 30 minutes, the resulting solution was centrifuged to remove insoluble materials, and the clear supernatant was separated. The supernatant was freeze-dried to obtain about 67 g of soluble zinc-aspartic acid chelate.

EXAMPLE 11

Preparation of Calcium-Glutamic Acid Chelate 20 g of calcium carbonate (calcium content: 38%) was dispersed in 500 ml of water and dissolved therein by stirring, and 60 g of glutamic acid was added thereto to perform a reaction, then the solution was continually stirred until the calcium carbonate and glutamic acid were entirely dissolved. Bubbles were generated in the initial stage of reaction but they disappeared after a certain time. The resulting reaction solution was centrifuged to remove insoluble materials, and the clear supernatant was separated. The supernatant was freeze-dried to obtain about 78 g of calcium-aspartic acid chelate.

EXAMPLE 12

Preparation of Magnesium-Glutamic Acid Chelate 20 g of calcium carbonate (calcium content: 38%) was dispersed in 500 ml of water and dissolved therein by siring, and 60 g of glutaric acid was added thereto to perform a reaction, the solution was continually stirred until the calcium carbonate and glutamic acid were entirely dissolved. Next, 30 g of magnesium sulfate (magnesium content: 9.86%) was added to the reaction mixture, and a white precipitate of calcium sulfate was formed. After incubating the reaction for 30 minutes, the resulting solution was centrifuged to remove insoluble materials, and the clear supernatant was separated. The supernatant was freeze-dried to obtain about 61 g of soluble magnesium-glutamic acid chelate.

EXAMPLE 13

Preparation of Calcium-Aspartic Acid Chelate 20 g of calcium carbonate (calcium content: 38%) was dispersed in 500 ml of water and dissolved therein by stirring, and 60 g of aspartic acid was added thereto to perform a reaction, then the solution was continually stirred until the calcium carbonate and aspartic acid were entirely dissolved. Bubbles were generated in the initial stage of reaction but they disappeared after a certain time. The resulting reaction solution was centrifuged to remove insoluble materials, and the clear supernatant was separated. The supernatant was freeze-dried to obtain about 78 g of calcium-aspartic acid chelate.

EXAMPLE 14

Preparation of Zinc-Aspartic Acid Chelate 20 g of calcium carbonate (calcium content: 38%) was dispersed in 500 ml of water and dissolved therein by stirring, and 60 g of aspartic acid was added thereto to perform a reaction, then the solution was continually stirred until the calcium carbonate and aspartic acid were entirely dissolved. Next 30 g of zinc sulfate (zinc content: 35%) was added to the reaction mixture, and a white precipitate of calcium sulfate was formed. After incubating the reaction for 30 minutes, the resulting solution was centrifuged to remove insoluble materials, and the clear supernatant was separated. The supernatant was freeze-dried to obtain about 67 g of soluble zinc-aspartic acid chelate.

EXAMPLE 15

Preparation of Zinc-Glutamic Acid Chelate 20 g of zinc carbonate (zinc content: 32%) was dispersed in 500 ml of water and dissolved therein by stirring, and 60 g of glutamic acid was added thereto to perform a reaction, then the solution was continually stirred until the zinc carbonate and glutamic acid were entirely dissolved. Bubbles were generated in the initial stage of the reaction but they disappeared after a certain time. The resulting reaction solution was centrifuged to remove insoluble materials, and the clear supernatant was separated. The supernatant was freeze-dried to obtain about 70 g of zinc-glutamic acid chelate (zinc content: 6.5%).

EXAMPLE 16

Preparation of Zinc-Aspartic Acid Chelate 20 g of zinc carbonate (zinc content: 32%) was dispersed in 500 ml of water and dissolved therein by stirring, and 60 g of aspartic acid was added thereto to perform a reaction, then the solution was continually stirred until the zinc carbonate and aspartic acid were entirely dissolved. Bubbles were generated in the initial stage of the reaction but they disappeared after a certain time. The resulting reaction solution was centrifuged to remove insoluble materials, and the clear supernatant was separated. The supernatant was freeze-died to obtain about 72 g of zinc-aspartic acid chelate.

EXAMPLE 17

Preparation of Iron-Aspartic Acid Chelate 20 g of calcium carbonate (calcium content: 38%) was dispersed in 500 ml of water and dissolved therein by stirring, and 60 g of aspartic acid was added thereto to perform a reaction, then the solution was continually stirred until the calcium carbonate and aspartic acid were entirely dissolved. Next, 30 g of ferrous sulfate (iron content: 20%) was added to the reaction mixture, and a white precipitate of calcium sulfate was formed. After incubating the reaction for 30 minutes, the resulting solution was centrifuged to remove insoluble materials, and the clear supernatant was separated. The supernatant was freeze-dried to obtain about 62 g of soluble iron-aspartic acid chelate.

EXAMPLE 18

Preparation of Mineral Complex-Glutamic Acid Chelate 20 g of calcium carbonate (calcium content: 38%) was dispersed in 500 ml of water and dissolved therein by siring, and 60 g of glutaric acid was added thereto to perform a reaction, then the solution was continually stirred until the calcium carbonate and glutamic acid were entirely dissolved. Next, 10 g of zinc sulfate, 1.5 g of manganese sulfate, 2 g of copper sulfate and 2.2 g of ferrous sulfate were added to the reaction mixture, and a white precipitate of calcium sulfate was formed. After incubating the reaction for 30 minutes, the resulting solution was centrifuged to remove insoluble materials, and the clear supernatant was separated. The supernatant was freeze-dried to obtain about 65 g of soluble mineral complex-glutamic acid chelate.

EXAMPLE 19

Experiment as to the Stability of Amino Acid Chelate

The following experiment was carried out to ascertain the stability of amino acid chelate compound, obtained in EXAMPLE 1, on its storage in an aqueous solution for a long time.

Preparation of Samples:
1) preparation of samples by adding the above amino acid chelate compound into distilled water adjusted to pH 3, 5, 7 and 9, respectively.
2) preparation of samples by adding the above amino acid chelate compound into solutions adjusted to pH 3, 5, 7 and 9 using buffer, respectively.
3) preparation of samples by adding the above amino acid chelate compound into selected commercially available beverages (MIEROFIBER® (Hyundai Pharm., Korea), BACCHUS® (Donga Pharm., Korea) and orange juice (HaeTae Beverage Corp., Korea)), respectively.
4) preparation of samples by adding the above amino acid chelate compound into selected commercially available cosmetics (ISA KNOX® (LG Chemical Corp., Korea), MAMONDE® (AmorePacific Corp., Korea))
5) preparation of samples by adding the above amino acid chelate compound into ALGI® (GG Tech. Co. Ltd., Korea) as a plant growth-accelerating agent The above samples were stored at 4, 25 and 50° C., respectively, and then tested for any precipitation or change in pH.

Even after maintenance for 3 months under the above conditions, there was no precipitation or remarkable change in pH. Accordingly, it was shown that the amino acid chelates prepared by the method according to the present invention are very stable compounds under the condition of various pHs and temperatures in various aqueous solutions.

EXAMPLE 20

Test of Properties

The amino acid chelate compound obtained in EXAMPLE 1 was added to a commercially available MIEROFIBER® beverage (Hyundai Pharm., Korea) to measure the effect of the former on the properties of the latter including taste and appearance. In order to test the effect of amino acid chelate compound when added to MIEROFIBER® at 1% by weight, ten specialists measured the taste and appearance of resulting samples and asked to provide a total rating thereof. The taste categories to be tested were glutamate taste and sour taste in which each taste was evaluated as 1 (very weak), 2 (weak), 3 (average), 4 (strong) and 5 (very strong). The appearance was also evaluated as 1 (very bad), 2 (bad), 3 (average), 4 (good) and 5 (very good) by measuring the color and clearness of the samples. The results in TABLE 3 below are the aggregate values as measured by the ten specialists. Symbols "+", "++", "+++" and "++++" express the range of the aggregate values, i.e., 10-19, 20-29, 30-39 and more than 40, and also mean "bad (weak)", "average", "good (strong)" and "very good (very strong)", respectively.

TABLE 3

| | Items of test | | | | |
| --- | --- | --- | --- | --- | --- |
| | Taste | | Appearance | | Overall |
| Objects of test | Glutamate taste | Sour taste | Color | Clearness | evaluation |
| Control group (MIEROFIBER ®) | 10 (+) | 11 (+) | 46 (++++) | 48 (++++) | 48 (++++) |
| Samples (MIEROFIBER + chelate of EX. 1) | 12 (+) | 11 (+) | 48 (++++) | 47 (++++) | 47 (++++) |

As seen in TABLE 3 above, it was ascertained that the amino acid chelate compound according to the present invention does not have any negative effect on the properties (taste, appearance, etc.) of a beverage to which the chelate compound is added.

EXAMPLE 21

Use of Amino Acid Chelate as Powdered Seasoning 0.5% by weight of penta-ribonucleotide was mixed with 99.5% by weight of the amino acid chelate compound obtained in EXAMPLE 1 to make a powdered seasoning. When the powdery seasoning was tasted, it was ascertained to exhibit the same taste as that of sodium glutamate as an existing powdered seasoning. Accordingly, the amino acid chelate compound according to the present invention may be used as a powdered seasoning.

EXAMPLE 22

Use of Amino Acid Chelate as Liquid Seasoning

A liquid mixture having a composition as in the below TABLE 4 was prepared and tasted. It was ascertained that the taste of the liquid mixture is the same as that of sodium glutamate as an existing seasoning. Accordingly, the chelate compound according to the present invention may be used as a liquid seasoning.

TABLE 4

| Components | Content |
|---|---|
| Vegetable protein hydrolysate (nitrogen content: 3%) | 10% |
| Concentrated tuna fish sauce | 4% |
| Liquid fructose | 6% |
| Purified water | 50% |
| Purified salts | 8% |
| Chelate compound of EX. 1 | 10% |
| Sugar | 5% |
| Xanthan gum | 0.3% |
| penta-nucleotide | 0.5% |
| Concentrated onion juice | 2% |
| Concentrated garlic juice | 1% |
| Concentrated beef juice | 1% |
| Purified beef tallow | 1% |
| Alcohol | 0.7% |
| Soluble pepper extract | 0.5% |

EXAMPLE 23

Application of Amino Acid Chelate to Milk

The amino acid chelate compound obtained in EXAMPLE 9 was mixed with orange juice at a composition as in the below TABLE 5 and then stored for a long time; however, no precipitates were formed and the taste was not changed.

TABLE 5

| Component | Content |
|---|---|
| Liquid fructose | 5% |
| Polydextrose | 1% |
| Citric acid | 5% |
| Vitamin C | 0.02% |
| Chelate compound of EX. 9 | 2% |
| Concentrated orange juice | 25% |
| Water | 67% |

EXAMPLE 25

Application of Amino Acid Chelate to Cosmetics-1

A skin lotion cosmetic composition containing the amino acid chelate compound obtained in EXAMPLE 8 at a composition as in the below TABLE 6 was prepared and then maintained for a long time; however, the resulting lotion was not discolored and did not have any negative effect when applied to skin.

TABLE 6

| Component | Content |
|---|---|
| 1,3-butylene glycol | 5% |
| Glycerine | 5% |
| EDTA-2Na | 0.02% |
| Trimethylglycine | 2.0% |
| Cetanol | 1.0% |
| Glyceryl monostearate emulsifier | 1.0% |
| Polysorbate 60 | 1.2% |
| Sorbitan sesquioleate | 0.3% |
| Cetyl 2-ethyl-hexaoate | 4.0% |
| Squalane | 5.0% |
| Dimethicone | 0.3% |
| Glyceryl stearate | 0.5% |
| Carbomer | 0.15% |
| Triethanolamine | 0.5% |
| Imidazolidinyl urea | 0.2% |
| Chelate compound of EX. 8 | 2.0% |
| Purified water | 71.8% |

EXAMPLE 26

Application of Amino Acid Chelate to Cosmetics-2

A liquid-type cosmetic containing the amino acid chelate compound obtained in EXAMPLE 8 at a composition as in the below TABLE 7 was prepared and then stored for a long time; however, the resulting cosmetic was not discolored and did not have any negative effect when applied to skin.

TABLE 6

| Component | Content |
|---|---|
| 1,3-butylene glycol | 4.0% |
| Dipropylene glycol | 5.0% |
| EDTA-2Na | 0.02% |
| Octyldodeceth-16 | 0.3% |
| PEG60 hydrogenate castor oil | 0.2% |
| Chelate compound of EX. 8 | 0.5% |
| Purified water | 90% |

EXAMPLE 27

Test of the Degree of Absorption of Amino Acid Chelate into the Body of Rat

1. Description of Experiment 3-week old Sprague-Dawley male rats (Daehan Biolink Co., Ltd., Korea) were employed for the present experiment after adjustment to an elementary diet These rats were divided into a normal group and an experimental group. The diet for the normal group ("normal diet") was prepared based upon AIN-76 diet composition, whereas the diet for the experimental group ("Ca-flee diet" or "experimental diet") was prepared by replacing a mineral mixture in the normal diet composition with a Ca deficient mineral mixture. After feeding the respective diets for 24 days, the experimental group was divided into (1) a Ca-flee control group fed no calcium, (2) a CaCO₃ control group fed CaCO₃ as a Ca-supplying agent, (3) a SW-Ca control group fed seaweed calcium as a Ca-supplying agent, and (4) a Asp-Ca group fed calcium-aspartic acid chelate obtained in EXAMPLE 13 as a Ca-supplying agent. These Ca-supplying agents were orally administered to each group along with the Ca-free diet for one week before the rats were sacrificed.

The concentration of Ca-supplying agent in the oral administration was ⅓ of the concentration of calcium in AIN-76 mineral mixture, which corresponds to 10 times the recommended amount for adult males. 3× distilled water was used for preparation of the experimental diet and was also was fed to rats for maintenance. The compositions of diets administered to the normal group and experimental groups, respectively, are described in TABLE 8 as below.

TABLE 8

Diet composition (g/kg diet)

| | Normal group | Experimental groups | | | |
|---|---|---|---|---|---|
| | | Ca-free | CaCO₃ | Asp-Ca | SW-Ca |
| Casein | 200 | 200 | 200 | 200 | 200 |
| Sucrose | 100 | 100 | 100 | 100 | 100 |
| Cellulose | 50 | 50 | 50 | 50 | 50 |
| Mineral mix[1] | 35 | 35 | 35 | 35 | 35 |
| Vitamin mix | 10 | 10 | 10 | 10 | 10 |
| DL-methionine | 3 | 3 | 3 | 3 | 3 |
| Choline bitartrate | 2.5 | 2.5 | 2.5 | 2.5 | 2.5 |
| Corn starch | 549.5 | 549.5 | 549.5 | 549.5 | 549.5 |
| Corn oil | 50 | 50 | 50 | 50 | 50 |
| (oral administration) | | | (mg/day) | | |
| CaCO₃ 40% | — | — | 80 | — | — |
| Asp-Ca 10.8% | — | — | — | 320 | — |
| Seaweed Ca 33% | — | — | — | — | 97 |

[1] normal group: AIN-76 Mineral mixture; experimental groups: Ca deficient mineral mixture The abdomens of the rats were cut open under ether anesthesia, then blood was harvested from abdominal aorta, and major organs such as liver, kidney, spleen, etc. were extend, followed by the extraction of fibula. The blood was centrifuged at 3000 rpm for 10 minutes to separate serum. Each organ and bone was trimmed and washed with normal saline and moisture on the surface thereof was removed to measure the weight and length thereof.

2. Measurement of Calcium

The content of calcium in serum and urine was measured by Calcium Reagent Arsenazo III kit (Sigma Corp., U.S.A). In order to measure the content of calcium in feces, the feces (sample) was put in a Pyrex beaker and the weight thereof was measured to 0.1 mg unit, then 5 ml of HNO₃ and 2 ml of H₂O₂ were added and the beaker was left uncovered on a hot plate. The acid-digested sample was cooled and 2 ml of H₂O₂ was added thereto, followed by heating. Next, the acid was sufficiently volatilized to make the concentration of HNO₃ to 1-5%, followed by the analysis with ICP-AES (inductively Coupled Plasma Atomic Emission Spectrometer). The condition for analysis is given below.

Model: Jobin Yvon 138 Ultrace
Source: Argon plasma (6000 K)
Spectral range: 160-800 nm
Resolution: 0.005 nm (UV)
Detection limit: 1×ppb~100×ppb
Wavelength for analysis: 393.366 nm 3. Effect On Weight of Major Organs TABLE 9 below shows the effect which the administration of each Ca-supplying agent to calcium-starved rats has on the weight of major organs. The weight of liver in the Ca-free control group was low compared to that of the normal group, whereas the weight of liver in the Asp-Ca group was almost the same as that of the normal group. The weights of kidney and spleen were not different among the groups.

TABLE 9

Liver, kidney and spleen weights

| | Liver (mg/BW) | Kidney (mg/BW) | Spleen (mg/BW) |
|---|---|---|---|
| Normal group | 44.75 ± 1.89 | 8.50 ± 0.29 | 3.50 ± 0.50 |
| Ca-free control group | 40.67 ± 1.41 | 8.83 ± 0.31 | 3.00 ± 0.00 |
| CaCO₃ control group | 37.40 ± 1.63 | 8.60 ± 0.40 | 3.00 ± 0.00 |
| Asp-Ca group | 44.17 ± 1.68 | 8.40 ± 0.26 | 3.00 ± 0.00 |
| SW-Ca control group | 36.00 ± 0.63 | 8.20 ± 0.20 | 3.00 ± 0.32 |

4. Effect on Weight and Length of Fibula

TABLE 10 as below shows the effect of Ca-supplying agent on the weight and length of fibula in Ca-starved rats. The weight of fibula in the Ca-free control group was about 32.5% less than the normal group, and when the Ca-supplying agents were administered (in the case of the CaCO₃ control group and Asp-Ca group), the weight of fibula was higher than in the Ca-free group, but did not come up to the level of the normal group. The length of fibula in the Ca-free control group was lower than that of the normal group, whereas the length of fibula in the CaCO₃ control group and Asp-Ca control group was higher than that of the Ca-free control group, wherein there was no significant difference between the CaCO₃ control group and Asp Ca control group. It has been shown previously that where the intake of calcium is not sufficient or the spongy bone does not hold sufficient calcium, the transfer of calcium from other bones to the pelvis and vertebra preferentially occurs, and as the intake of calcium increases, the size of spongy bone increases. This phenomenon demonstrates the result of the present experiment, showing that while the weight and length of fibula decrease due to the deficiency of calcium, they increase by the administration of Ca-supplying agents.

TABLE 10

Weight and length of fibula

| | Weight of fibula (g) | Length of fibula (mm) |
|---|---|---|
| Normal group | 0.403 ± 0.015 | 32.28 ± 0.44 |
| Ca-free control group | 0.272 ± 0.032 | 29.01 ± 1.06 |
| CaCO₃ control group | 0.332 ± 0.033 | 30.03 ± 1.10 |
| Asp-Ca group | 0.327 ± 0.031 | 30.88 ± 1.87 |
| SW-Ca control group | 0.292 ± 0.043 | 28.83 ± 1.49 |

5. Concentration of Calcium in Serum Urine and Feces

TABLES 11 and 12 below show the effect of Ca-supplying agents on the concentration of calcium in serum, urine and feces of calcium-starved rats. Where the concentration of calcium in blood decreases, calcium is eluted from bones by the function of parathyroid hormone; therefore, the concentration of calcium in blood is a very important physiological factor for maintenance of the normal skeletal metabolism and bone weight. The result of the present experiment shows that the concentration of calcium in blood in the Ca-free control group is significantly lower than in the normal group, but is higher in groups administered with Ca-supplying agents. Especially, the concentration of calcium in blood in the Asp-Ca group and SW-Ca control group are approximately equal to the normal group. Likewise, the concentration of calcium in urine in the Ca-free control group is about 45% less than that of the normal group, but approximately equal to the normal group in groups administered with Ca-supplying agents.

TABLE 11

Concentration of calcium in serum and urine

|  | Serum (mg/dl) | Urine (mg/dl) |
|---|---|---|
| Normal group | 10.68 ± 0.18 | 0.20 ± 0.03 |
| Ca-free control group | 8.12 ± 0.52 | 0.11 ± 0.03 |
| CaCO₃ control group | 9.13 ± 0.21 | 0.22 ± 0.01 |
| Asp-Ca group | 10.63 ± 0.21 | 0.22 ± 0.04 |
| SW-Ca control group | 10.44 ± 0.07 | 0.32 ± 0.02 |

TABLE 12

Concentration of serum-calcium in blood collected from eyeball

|  | Serum (mg/dl) |
|---|---|
| Normal group | 12.19 ± 0.38 |
| Ca-free control group | 8.60 ± 0.51 |
| CaCO₃ control group | 8.52 ± 0.27 |
| Asp-Ca group | 11.24 ± 0.85 |

6. Absorption of Calcium

When the content of calcium in feces of rat, i.e., the amount of excreted calcium, was measured, it was the highest in the $CaCO_3$ control group and the second highest in the SW-Ca control group and the lowest in the Asp-Ca group, respectively. In terms of relative absorption, the $CaCO_3$ control group did not show any positive absorption (0%) and the SW-Ca control group showed 28.8%. Meanwhile, the Asp-Ca group showed 65.9%, which is more than double that of the SW-Ca control group.

TABLE 13

Relative absorption of calcium

|  | Ca intake feces (mg/3days) | Ca excretion in (mg/3days) | Relative absorption (%) |
|---|---|---|---|
| Ca-free control group | 0 | 2.69 | — |
| CaCO₃ control group | 96 | 98.68 | 0 |
| Asp-Ca group | 96 | 35.39 | 65.9 |
| SW-Ca control group | 96 | 71.05 | 28.8 |

EXAMPLE 27

Effect of Amino Acid Iron Chelate on the Absorption of Fe in Fe-Starved Rat

1. Description of Experiment 3-week old Sprague-Dawley male rats (Daehan Biolink Co., Ltd., Korea) were employed for the present experiment after application of an elementary diet for one week. These rats were divided into a normal group and an experimental group. The diet for the normal group ("normal diet") was prepared based upon AIN-76 diet composition, whereas the diet for the experimental group ("Fe-free diet" or "experimental diet") was prepared by replacing a mineral mixture in the normal diet composition with a Fe-deficient mineral mixture. After feeding the normal diet and Fe-flee diet to the normal group and experimental group for 24 days, respectively, the experimental group was divided into (1) Fe-starved control group, (2) Heme control group fed Heme iron as a Fe-supplying agent, and (3) Fe-Asp group fed the iron-aspartic acid chelate obtained in EXAMPLE 17 as a Fe-supplying agent. These Fe-supplying agents were orally administered to rats along with the experimental diet for one week before the rats were sacrificed.

The concentration of Fe-supplying agent for the oral administration was 10 times the recommended amount for adult males. 3× distilled water was used for preparation of the experimental diet and was fed to rats for maintenance. The compositions of diets administered to the normal group and experimental group, respectively, are described in TABLE 14 below.

TABLE 14

Diet composition (g/kg diet)

| | Experimental group | | | |
|---|---|---|---|---|
|  | Normal group | Fe-free control group | Heme control group | Fe-Asp group |
| Casein | 200 | 200 | 200 | 200 |
| Sucrose | 100 | 100 | 100 | 100 |
| Cellulose | 50 | 50 | 50 | 50 |
| Mineral mixture[1] | 35 | 35 | 35 | 35 |
| Vitamin mixture | 10 | 10 | 10 | 10 |
| DL-methionine | 3 | 3 | 3 | 3 |
| Choline bitartrate | 2.5 | 2.5 | 2.5 | 2.5 |
| Corn starch | 549.5 | 549.5 | 549.5 | 549.5 |
| Corn oil | 50 | 50 | 50 | 50 |
| (oral administration) | | (mg/ml/day) | | |
| 1% heme | — | — | 50 | — |
| 10% Fe-Asp | — | — | — | 5 |

[1]normal group: AIN-76 mineral mixture; experiment groups: Fe deficient mineral mixture Rats were adapted to a cage for one week before the start of the experiment, and their feces were collected for a final 3 days. On the final day, the abdomen was cut open under ether anesthesia, then blood was harvested from abdominal aorta, and major organs such as liver, kidney, spleen, etc. were extracted. Half of the harvested blood was put in a vacutainer containing 7.5% EDTA $K_3$ to prevent coagulation, and the remaining blood was centrifuged at 3000 rpm for 10 minutes to separate serum. Each organ was trimmed and washed with normal saline, then moisture on the surface thereof was removed to measure the weight and length.

2. Measurement

CBC (Complete Blood Count: Red blood cell; RBC, white blood cell; WBC, Hematocrits; HCT, Hemoglobin; Hb) was measured from the anticoagulated blood, and IRON and TIBC Total Iron Binding Capacity) were measured from the blood serum. CBC was measured by an automatic analyzer (ADVIA 120, Bayer, U.S.A). As reagents, Isoton III (Beckman Coulter, U.S.A), Coulter clenz (Beckman Coulter), Lyse S III (Beckman Coulter), 4% sodium hypochloride-solution (Beckman Coulter) and 4C-plus (Beckman Coulter), Scatter Pak (Beckman Coulter) were used. IRON was measured by an automatic biochemical analyzer (HITACHI 71501, Japan) according to the Nitrose-PSAP direct method, and SICDIA Fe-750 REAGENT (YongYeon Chemical Corp., Korea) was used as a reagent. TIBC was measured by a biochemical analyzer (HITACHI 7150, Korea) using Kit-TIBC (RM 176-K®, Eiken, Japan).

3. Statistical Analysis

All data obtained in the present experiment were expressed with the mean standard error using the SAS program. T-test in each group was carried out at a range of $P<0.05$ by Duncan's multiple comparison test.

4. Measurement of Weight of Major Organs

TABLE 15 shows the effect which the admiration of each Fe-supplying agent to Fe-starved rats has on the weight of major organs. The weight of liver in the Fe-free control group was not significantly different from that of the normal group. Likewise, there were no significant differences between groups in view of the weights of kidney and spleen. However, the Fe-Asp group in which Fe-Asp was administered as a Fe-supplying agent exhibited a numerical value nearest to that of the normal group.

TABLE 15

Liver, Kidney and Spleen weight of rat

| | Liver (mg/BW) | Kidney (mg/BW) | Spleen (mg/BW) |
|---|---|---|---|
| Normal group | 39.25 ± 0.85 | 7.50 ± 0.29 | 3.00 ± 0.41 |
| Fe-free control group | 39.90 ± 0.90 | 7.30 ± 0.21 | 2.70 ± 0.15 |
| Heme control group | 36.90 ± 1.06 | 7.20 ± 0.13 | 2.78 ± 0.15 |
| Fe-Asp group | 40.60 ± 1.00 | 7.50 ± 0.22 | 3.00 ± 0.15 |

5. Content of Iron and TIBC in Serum

Fe-supplying agent was periodically administered to Fe-starved rats, and after a certain number of days, IRON and TIBC in blood were measured. As seen in TABLE 16 below, the amount of IRON in the normal group was highest and the amount of IRON in the Fe-free control group was quite low. The values of IRON in the Heme control group and Fe-Asp group were lower than that of the normal group but were significantly higher than that of the Fe-free control group. In view of the value of TIBC, i.e., total iron binding capacity, the Fe-free control group had significantly higher TIBC than the normal group. The value of TIBC in the Heme control group was similar to that of the Fe-free control group. The value of TIBC in the Fe-Asp group did not approach that of the normal group but was lower than that of the Fe-free control group. Further, TS (transferrin saturation) was also measured; the value of TS in the Fe-free control group was significantly lower than that of the normal group, whereas this was higher in groups administered with Fe-supplying agents. The value of TS in the Fe-Asp group was higher than that of the Heme control group.

TABLE 16

Concentration of IRON and TIBC in serum

| | IRON (µg/dl) | TIBC (µg/dl) | TS (%) |
|---|---|---|---|
| Normal group | 224.50 ± 33.65 | 662.75 ± 17.02 | 33.87 |
| Fe-free control group | 96.13 ± 10.27 | 841.90 ± 13.90 | 11.42 |
| Heme control group | 140.8. ± 25.55 | 824.63 ± 11.60 | 17.07 |
| Fe-Asp group | 175.2 ± 24.61 | 735.44 ± 9.30 | 23.82 |

6. Change of Concentrations of Blood Hemoglobin and Hematocrit

TABLE 17 below shows the effect which the administration of Fe-supplying agents to Fe-starved rats has on the concentrations of RBC (red blood cells), WBC (white blood cells), Hb (hemoglobin), HCT (hematocrit), etc. in Firstly, the concentration of Hb in the Fe-free control group was significantly lower than that of the normal group. The concentration of Hb in the Heme control group was similar to that of the Fe-free control group. The concentration of Hb in the Fe-Asp group did not approach that of the normal group but was significantly higher than that of the Fe-free control group. These results demonstrate that the administration of Fe-Asp as a Fe-supplying agent helps the recovery of the Fe-deficient condition. Secondly, the HCT in the Heme control group and Fe-Asp group were high compared to that of the Fe-free control group, wherein the HCT in the Fe-Asp group approached the level of the normal group. This result demonstrates that Fe-Asp is a Fe-supplying agent very effective for recovering the Fe deficient condition. Furthermore, the present experiment was based upon the administration of Fe-supplying agent for 7 days; therefore, if the period of the administration is lengthened, the above effect would be expected to be even more remarkable.

TABLE 17

Concentrations of RBC, WBC, Hb and HCT

| | RBC ($\times 10^6$/mm$^3$) | WBC ($\times 10^3$/mm$^3$) | Hb (g/dl) | HCT (%) |
|---|---|---|---|---|
| Normal group | 7.47 ± 0.16 | 6.13 ± 0.50 | 13.96 ± 0.42 | 44.20 ± 1.43 |
| Fe-free control group | 6.90 ± 0.20 | 7.55 ± 0.36 | 11.18 ± 0.38 | 35.40 ± 1.28 |
| Heme control group | 7.01 ± 0.16 | 6.12 ± 0.37 | 11.17 ± 0.28 | 36.11 ± 0.89 |
| Fe-Asp group | 7.32 ± 0.35 | 6.02 ± 0.46 | 12.71 ± 0.49 | 39.33 ± 1.86 |

7. Absorption Degree of Iron

When the content of iron in feces of rats was measured, the content of iron excreted in the Heme control group was significantly higher Man that of the Fe-Asp group. In view of relative absorption of iron, the Heme control group showed absorption of 21.3%, whereas the Fe-Asp group showed absorption of 50.2% which is more than two times of that of the Heme control group.

TABLE 18

Relative iron absorption

| | Fe intake (µg/3days) | Fecal Fe excretion (µg/3days) | Relative absorption (%) |
|---|---|---|---|
| Fe-free control group | 0 | 247.4 | — |
| Heme control group | 1500 | 1427.4 | 21.3 |
| Fe-Asp group | 1500 | 1000.6 | 50.2 |

INDUSTRIAL APPLICABILITY

As described above, in accordance with the method of the present invention, metallic amino acid chelates that are electrically neutral and free of interfering ions can readily be made. Moreover, when added to a product such as medical supplies, foods, beverages, cosmetics, feeds, etc., these amino acid chelates are stable at a variety of temperature and pH ranges and also have no effect on the properties of the products, including taste and appearance.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. A method for preparation of an amino acid chelates, comprising the step of reacting a naturally occurring or synthetic metal carbonate with an acidic amino acid in an aqueous solution, wherein the metal carbonate is one or more carbonates with a valence of 2 or more selected from the group consisting of calcium carbonate, copper carbonate, zinc carbonate, ferrous carbonate, cobalt carbonate, chromium carbonate, magnesium carbonate and manganese carbonate; and the acidic amino acid is glutamic acid, aspartic acid or a combination thereof.

2. The method according to claim 1, wherein the metal carbonate is a naturally occurring metal carbonate.

3. The method according to claim 1, wherein the metal carbonate is calcium carbonate.

4. The method according to claim 3, wherein the calcium carbonate is derived from a naturally occurring source.

5. The method according to claim 1, wherein the amount of the metal carbonate and acidic amino acid used in the reaction is in a molar ratio of 1:1~1:4 (metal carbonate: acidic amino acid); the reaction temperature is in the range of 0~100° C.; and the reaction pH is adjusted to 4~7 at the time of termination of reaction.

6. The method according to claim 5, wherein the pH is adjusted to 4.5~6.5.

7. The method according to claim 1, wherein a metal sulfate is further added at the same time as the initiation of carbonate-amino acid reaction, or during the reaction, or after the termination of the reaction, thereby performing an additional reaction.

8. The method according to claim 7, wherein the metal sulfate is added during the carbonate amino acid reaction or after the termination of the reaction to perform the additional reaction.

9. The method according to claim 7, wherein the metal sulfate is one or more sulfates selected from the group consisting of calcium sulfate, magnesium sulfate, zinc sulfate, copper sulfate, ferrous sulfate, manganese sulfate, chromium sulfate and cobalt sulfate, and also contains a metal ion different from the metal ion of the metal carbonate.

10. The method according to claim 7, wherein the amount of the metal sulfate used for the additional reaction is in a molar ratio of 1:1~1:4 (metal sulfate carbonate-amino acid chelate) in which the carbonate-amino acid chelate is obtained from a reaction of the metal carbonate and acidic amino acid.

11. The method according to claim 1, further comprising administering the amino acid chelate in a sitologocally effective amount as a pharmaceutical composition, wherein the amino acid chelate is one or more selected from the group consisting of calcium glutamate/aspartate, calcium bisglutamate, calcium bisaspartate, copper glutamate/aspartate, copper bisglutamate, copper bisaspartate, zinc glutamate/aspartate, zinc bisglutamate, zinc bisaspartate, iron glutamate/aspartate, iron bisglutamate, iron bisaspartate, iron bisglutamate/aspartate, iron glutamate/bisaspartate, chromium glutamate/aspartate, chromium bisglutamate, chromium bisaspartate, chromium bisglutamate/aspartate, chromium glutamate/bisaspartate, cobalt glutamate/aspartate, cobalt bisglutamate, cobalt bisasparate, magnesium glutamate/aspartate, magnesium bisglutamate, magnesium bisaspartate, manganese glutamate/aspartate, manganese bisglutamate, and manganese bisaspartate.

12. The method according to claim 1, further comprising administering the amino acid chelate in a cosmetically effective amount as a cosmetic the amino acid chelate is one or more selected front the group consisting of calcium glutamate/aspartate, calcium bisglutamate, calcium bisaspartate, copper glutamate/aspartate, copper bisaspartate, copper bisaspartate, zinc glutamate/aspartate, zinc bisglutamate, zinc bisaspartate, iron glutamate/aspartate, iron bisglutamate, iron bisaspartate, iron bisglutamate/aspartate, iron glutamate/bisaspartate, chromium glutamate/aspartate, chromium bisglutamate, chromium bisaspartate, chromium bisglutamate/aspartate, chromium glutamate/bisaspartate, cobalt glutamate/aspartate, cobalt bisglutamate, cobalt bisasparate, magnesium glutamate/aspartate, magnesium bisglutamate, magnesium bisaspartate, manganese glutamate/aspartate, manganese bisglutamate, and manganese bisaspartate.

13. The method according to claim 4, wherein the naturally occurring source is one or more selected from the group consisting of seaweed calcium, eggshell calcium, shell calcium and cuttlebone.

* * * * *